United States Patent [19]
Rao

[11] Patent Number: 5,866,730
[45] Date of Patent: Feb. 2, 1999

[54] PROCESS FOR ENRICHING 1,2-DICHLORO-1,1,2,2-TETRAFLUOROETHANE FROM A MIXTURE OF DICHLOROTETRAFLUOROETHANE ISOMERS

[75] Inventor: V. N. Mallikarjuna Rao, Wilmington, Del.

[73] Assignee: E. I. du Pont de Nemours and Company, Wilmington, Del.

[21] Appl. No.: 42,200

[22] Filed: Apr. 2, 1993

[51] Int. Cl.[6] .................................................. C07C 17/38
[52] U.S. Cl. ......................... 570/178; 570/170; 570/177
[58] Field of Search ...................... 570/177, 178, 570/170

[56] References Cited

U.S. PATENT DOCUMENTS

| | | | |
|---|---|---|---|
| 1,978,840 | 10/1934 | Henne | 260/162 |
| 2,005,708 | 6/1935 | Daudt et al. | 260/162 |
| 2,007,198 | 7/1935 | Henne | 260/162 |
| 2,062,743 | 12/1936 | Daudt et al. | 260/162 |
| 2,478,362 | 8/1949 | Benning | 202/51 |
| 2,598,411 | 5/1952 | Miller et al. | 260/653 |
| 2,755,313 | 7/1956 | Calfee et al. | 260/653 |
| 3,087,974 | 4/1963 | Hauptschein et al. | 260/653 |
| 3,157,707 | 11/1964 | Clark et al. | 260/653.7 |
| 3,258,500 | 6/1966 | Swamer et al. | 260/653.7 |
| 3,398,202 | 8/1968 | Foulletier | |
| 3,541,165 | 11/1970 | Vecchio et al. | 260/653.4 |
| 3,632,834 | 1/1972 | Christoph et al. | 260/653.7 |
| 3,650,987 | 3/1972 | Vecchio et al. | 252/422 |
| 3,752,850 | 8/1973 | Scherer et al. | 260/544 F |
| 3,754,043 | 8/1973 | Bjornson et al. | |
| 3,755,477 | 8/1973 | Firth et al. | 260/653.4 |
| 4,319,060 | 3/1982 | Cunningham et al. | 570/177 |
| 4,439,534 | 3/1984 | Foulletier | 502/8 |
| 4,474,895 | 10/1984 | Foulletier | 502/181 |
| 4,605,798 | 8/1986 | Abel et al. | 570/164 |
| 4,766,260 | 8/1988 | Manzer et al. | 570/168 |
| 4,902,838 | 2/1990 | Manzer et al. | 570/151 |
| 5,036,036 | 7/1991 | Lerou | 502/317 |
| 5,055,624 | 10/1991 | Lantz et al. | 570/167 |

FOREIGN PATENT DOCUMENTS

| | | |
|---|---|---|
| 685511 | 11/1966 | Belgium . |
| 760001 | 5/1967 | Canada ................................. 570/177 |
| 2025145 | 9/1990 | Canada . |
| 0 426 343 A1 | 5/1991 | European Pat. Off. . |
| 1668346 | 10/1973 | Germany . |
| SHO 51-59804 | 5/1976 | Japan . |
| 1 578 933 | 11/1980 | United Kingdom . |
| 9218 446 | 10/1992 | WIPO . |

OTHER PUBLICATIONS

J. M. Hamilton, Jr., *Adv. In Flourine Chem.*,3:117–180 (1963).

Glajch et al., Column Packings for On–Line GC Analysis of Fluorocarbons in the Presence of Reactive Gases, *LC–GC*, 4, No. 6, 574–577, 1989.

*Primary Examiner*—Alan Siegel

[57] ABSTRACT

A process is disclosed for enriching the amount of CFC-114 relative to the amount of CFC-114a from an initial mixture containing both isomers, by contacting said initial mixture with hydrogen chloride in the vapor phase at an elevated temperature in the presence of a catalyst to produce a product mixture containing $C_2Cl_2F_3$ and chlorination products of $CCl_2FCF_3$ wherein the weight ratio of $CClF_2CClF_2$ to the total $C_2Cl_2F_4$ is higher than the weight ratio of $CClF_2CClF_2$ to the total $C_2Cl_2F_4$ in the initial mixture. The chlorination products of CFC-114a (e.g., $CCl_3CF_3$) in the product mixture may then be separated from the $C_2Cl_2F_4$ therein (e.g., by distillation).

14 Claims, No Drawings

5,866,730

PROCESS FOR ENRICHING 1,2-DICHLORO-1,1,2,2-TETRAFLUOROETHANE FROM A MIXTURE OF DICHLOROTETRAFLUOROETHANE ISOMERS

FIELD OF THE INVENTION

This invention relates to halocarbon isomer enrichment, and more particularly, to a process for enriching compositions containing $CClF_2CClF_2$ (i.e., CFC-114) relative to their $CCl_2FCF_3$ (i.e., CFC-114a) content.

BACKGROUND

Products containing isomers of $C_2Cl_2F_4$ are produced in various degrees of isomer purity. For example, $C_2Cl_2F_4$ can be produced by the chlorofluorination of perchloroethylene, and the product typically consists of a mixture of the isomers, $CClF_2CClF_2$ and $CCl_2FCF_3$ (see e.g., U.S. Pat. No. 4,605,798). If the $C_2Cl_2F_4$ isomer mixture is then used to produce $CHClFCF_3$ (HCFC-124), $CHF_2CClF_2$ (HCFC-124a), $CHF_2CHF_2$ (HFC-134) and/or $CH_2FCF_3$ (HFC-134a) by hydrodehalogenation, the products often consist of a mixture of $C_2HClF_4$ isomers and $C_2H_2F_4$ isomers. GB 1,578,933 illustrates that mixtures of $C_2Cl_2F_4$ isomers in ratios of CFC-114 to CFC-114a of about 28:1 to 1:1 can be hydrogenolyzed over a palladium on carbon catalyst to mixtures of $C_2H_2F_4$ isomers in ratios of HFC-134 to HFC-134a of from less than 0.01:1 to about 4:1, depending on reaction conditions. Over a palladium on alumina catalyst mixtures having CFC-114 to CFC-114a ratios of about 3:1 to 1:1 are essentially completely hydrogenolyzed to HFC-134a. PCT International Application No. 9218446 discloses that mixtures of $C_2Cl_2F_4$ isomers can be converted to mixtures of $C_2H_2F_4$ isomers with the product containing essentially the same distribution of fluorine atoms as the starting materials.

$C_2HClF_4$ isomers and $C_2H_2F_4$ isomers are used as refrigeration fluids for a number of applications. $C_2HClF_4$ isomers, like $C_2Cl_2F_4$ isomers, are also valuable raw material feeds for a number of other commercial processes. It has been found that for many of these applications, the presence of the unwanted isomer of an isomer pair can alter the physical properties of the desired product. As a result, there have been continually increasing market and process demands for high isomer purity materials. Identification of methods for enriching a composition's content of one isomer over another represents a significant aspect of preparing products for specific applications.

Purification of fluorocarbon products has been the subject of considerable research. Of particular interest are the challenges presented in separating fluorocarbon products from materials such as impurities in the starting materials used to produce the fluorocarbon products; and in separating excess reactants, and reaction co-products and by-products which are difficult to remove by standard separation methods such as distillation. Enrichment of CFC-114 in the presence of its isomer, CFC-114a, by distillation is not considered practical since their boiling points are close; the boiling point of CFC-114 is 3.6° C., and the boiling point of CFC-114a is 3.3° C.

SUMMARY OF THE INVENTION

This invention provides a process for enriching the amount of 1,2-dichloro-1,1,2,2-tetrafluoroethane relative to the amount its isomer, 1,1-dichloro-1,2,2,2-tetrafluoroethane, from an initial mixture containing them. The process comprises contacting the initial mixture with hydrogen chloride in the vapor phase at an elevated temperature in the presence of a catalyst to produce a product mixture containing dichlorotetrafluoroethane ($C_2Cl_2F_4$) and chlorination products of $CCl_2FCF_3$ wherein the weight ratio of $CClF_2CClF_2$ to the total $C_2Cl_2F_4$ is higher than the weight ratio of $CClF_2CClF_2$ to the total $C_2Cl_2F_4$ in the initial mixture. The chlorination products of $CCl_2FCF_3$ in the product mixture may then be separated from the $C_2Cl_2F_4$ therein (e.g., by distillation).

DETAILED DESCRIPTION

The present invention involves selectively reacting 1,1-dichloro-1,2,2,2-tetrafluoroethane ($CCl_2FCF_3$) with HCl in the presence of its isomer, 1,2-dichloro-1,1,2,2-tetrafluoroethane ($CClF_2CClF_2$) in the vapor phase in the presence of a catalyst. The process is especially useful for enriching $CClF_2CClF_2$ from initial mixtures wherein the $CCl_2FCF_3$ content is equal to or greater than the $CClF_2CClF_2$ content. Preferably, the fraction of total $C_2Cl_2F_4$ which is $CCl_2FCF_3$ is reduced by at least about 25%. The initial mixture may consist essentially of $C_2Cl_2F_4$ isomers, or may contain other compounds which do not interfere with the selective reaction of $CCl_2FCF_3$. Typically, the reaction is controlled to provide $CCl_3CF_3$ as the major chlorination product of $CCl_2FCF_3$.

Oxygen may be present in some process embodiments. However, the mole ratio of oxygen to total $C_2Cl_2F_4$ during the contacting step is generally less than 1:1. Indeed, oxygen may be absent. Where oxygen is added, it may be fed to the reactor as such, or it may be diluted with an inert gas such as nitrogen, helium or argon. The source of the oxygen may also be air containing molecular oxygen. Chlorine may be present in some process embodiments, either as an initial reactant or as an in-situ formed product.

Suitable catalysts which can be used for selectively reacting CFC-114a with HCl in the presence of CFC-114 include vapor phase fluorination catalysts. Catalysts which may be used in accordance with this invention include alumina; fluorided alumina; aluminum fluoride; metals supported on alumina; metals supported on aluminum fluoride; magnesium fluoride supported on aluminum fluoride; metals supported on fluorided alumina; alumina on carbon; aluminum fluoride on carbon; fluorided alumina on carbon; metals supported on carbon; chromium catalysts; mixtures of metal halides, aluminum fluoride, and graphite; and chromium-magnesium optionally supported on graphite. Suitable metals include chromium, Group VIII metals (e.g., iron, cobalt and/or nickel), Group VIIB metals (e.g., manganese), Group IIIB metals (e.g., lanthanum), and zinc. Preferably, when used on a support, the total metal content of the catalyst will be from about 0.1 to 20 percent by weight; typically from about 0.1 to 10 percent by weight. Preferred supports include aluminum fluoride, fluorided alumina, and mixtures thereof.

Fluorided alumina and aluminum fluoride can be prepared as described in U.S. Pat. No. 4,902,838. Metals on aluminum fluoride and metals on fluorided alumina can be prepared by procedures described in U.S. Pat. No. 4,766,260. Catalysts comprising chromium are well known in the art, e.g. see U.S. Pat. No. 5,036,036. Chromium supported on alumina can be prepared as described in U.S. Pat. No. 3,541,165. Chromium supported on carbon can be prepared as described in U.S. Pat. No. 3,632,834. Catalysts comprising chromium and magnesium may be prepared as described in Canadian Pat. No. 2,025,145. Other metals and magnesium optionally on graphite can be prepared in a similar manner to the latter patent. Preferred catalysts include catalysts comprising aluminum fluoride.

The reaction of mixtures of $CClF_2CClF_2$ and $CCl_2FCF_3$ with HCl in the presence of the catalysts of the instant invention is normally conducted at about 200° C. to 325° C., preferably about 200° C. to 275° C., with a contact time of about 1 to about 120 seconds, preferably about 5 to about 60 seconds.

The amount of HCl should be at least a stoichiometric amount. Typically, the molar ratio of HCl to the $C_2Cl_2F_4$ isomer mixtures is within the range of from about 2:1 to about 100:1, and is preferably from about 3:1 to 50:1, and more preferably from about 5:1 to 20:1.

In general, with a given catalyst composition, the higher the temperature and the longer the contact time, the greater is the conversion of the $C_2Cl_2F_4$ isomer mixtures to polychlorinated products. The above variables can be balanced, one against the other, so that the reaction of $CCl_2FCF_3$ in the presence of $CClF_2CClF_2$ is maximized.

The reaction products are separated by conventional techniques, such as distillation. Some of the reaction products will have desired properties for commercial use. For example $CCl_3CF_3$ (CFC-113a) can be used to prepare CFC-114a which can then be converted to $CH_2FCF_3$ (HFC-134a) by hydrodechlorination. Others, such as $CCl_2=CCl_2$ can be recycled back to reactors which are being used for the synthesis of halofluorocarbons.

The reaction of the $C_2Cl_2F_4$ isomers with HCl may be conducted in any suitable reactor, including fixed and fluidized bed reactors. The reaction vessel should be constructed from materials which are resistant to the corrosive effects of hydrogen fluoride such as Inconel™ nickel alloy and Hastelloy™ nickel alloy.

Preferably, the CFC-114 in the product mixture is at least 95% of the total $C_2Cl_2F_4$ content. If, after separation, the relative amount of CFC-114 is lower than desired, the CFC-114 content can be further enriched by further reacting CFC-114a with HCl in accordance with this invention (e.g., by recycle or staging).

Pressure is not critical. Atmospheric and superatmospheric pressures are the most convenient and are therefore preferred.

Practice of the invention will be come further apparent from the following non-limiting examples.

EXAMPLE 1

Catalyst Activation

A reactor (a 0.5 inch (1.3 cm) ID, 12 inch (30.5 cm) long Inconel™ nickel alloy pipe) was charged with 21.0 g (30 mL) of gamma-alumina (1/12" (2.1 mm) extrudates) and placed in a sand bath. The bath was gradually heated to 175° C. while $N_2$ gas at a flow rate of 50 cc/min was passed through the reactor to remove traces of water. HF (50 cc/min) as well as nitrogen were then passed through the reactor for 4.3 hours at a 175° C. bath temperature. The reactor temperature was gradually raised to 400° C. over 4 hours while continuing to pass HF (80 cc/min) and nitrogen (20 cc/min) over the catalyst. At this point the temperature was reduced to 350° C., the HF stopped, and nitrogen flow continued until the catalyst was used.

A mixture containing $CClF_2CClF_2$ (CFC-114, 44.1%) and $CCl_2FCF_3$ (CFC-114a, 55.7%) and HCl was fed to the reactor. The $HCl:C_2Cl_2F_4$ molar ratio was 20:1, the reaction temperature varied between 250° and 350° C., and the contact time (C.T.) was 15 seconds. The results of these runs, in mole % are shown in Table 1.

TABLE 1

| Temp °C. | 114[a] | 114a[b] | 113[c] | 113a[d] | 112/a[e] | 111[f] | PCE[g] | Others[h] | $\frac{114}{114 + 114a}$ |
|---|---|---|---|---|---|---|---|---|---|
| Feed | 44.1 | 55.7 |  |  |  |  |  | 0.2 | 44.2 |
| 250 | 44.3 | 24.0 | 0.1 | 31.2 | 0.2 |  |  | 0.2 | 64.9 |
| 275 | 44.1 | 15.9 | 0.3 | 38.1 | 0.9 | 0.2 | 0.1 | 0.4 | 73.4 |
| 300 | 39.6 | 14.8 | 1.4 | 38.0 | 3.9 | 0.4 | 0.9 | 1.0 | 72.9 |
| 325 | 26.6 | 19.5 | 2.2 | 41.1 | 5.1 | 0.5 | 3.4 | 1.6 | 57.6 |
| 350 | 8.5 | 25.4 | 2.9 | 44.3 | 5.4 | 0.4 | 7.7 | 5.4 | 25.1 |

[a]114 is $CClF_2CClF_2$
[b]114a is $CCl_2FCF_3$
[c]113 is $CCl_2FCClF_2$
[d]113a is $CCl_3CF_3$
[e]112/a is $CCl_2FCCl_2F + CCl_3CClF_2$
[f]111 is $CCl_3CCl_2F$
[g]PCE is $CCl_2=CCl_2$
[h]Others includes $CClF_3$ and $C_2ClF_5$ Comparison of the data presented in Table 1 shows that for a given HCl/organic ratio and contact time, the 114/(114+114a) ratio increases with temperature up to a certain point and then decreases with increasing temperature.

A second series of runs was done with a commercially available mixture containing $CClF_2CClF_2$ (CFC-114, 87.9%) and $CCl_2FCF_3$ (CFC-114a, 12.1%) and HCl was fed to the reactor. The $HCl:C_2Cl_2F_4$ molar ratio was varied from 5:1 to 20:1, the reaction temperature varied between 200 and 275° C., and the contact time (C.T.) was varied from 15 to 60 seconds. The results of these runs, in mole % are shown in Table 2.

TABLE 2

| Temp °C. | HCl/Org. | CT | 114 | 114a | 113 | 113a | 112/a | 111 | PCE | Others | 114/(114 + 114a) |
|---|---|---|---|---|---|---|---|---|---|---|---|
| FEED |  |  | 87.9 | 12.1 |  |  |  |  |  |  | 87.9 |
| 200 | 20 | 45 | 87.3 | 1.4 |  | 10.9 | 0.3 | 0.1 |  |  | 98.4 |
| 225 | 20 | 30 | 86.3 | 1.5 | 0.1 | 10.6 | 0.8 | 0.3 | 0.3 | 0.1 | 98.3 |
| 225 | 10 | 30 | 87.2 | 2.1 | 0.1 | 9.8 | 0.6 | 0.1 |  | 0.1 | 97.7 |
| 225 | 5 | 30 | 88.0 | 3.1 | 0.1 | 8.4 | 0.3 |  |  | 0.1 | 96.6 |
| 250 | 20 | 30 | 81.8 | 2.4 | 0.5 | 11.7 | 2.3 | 0.7 | 0.6 |  | 97.2 |
| 250 | 10 | 30 | 83.9 | 2.8 | 0.4 | 10.7 | 1.6 | 0.4 | 0.2 |  | 96.8 |
| 250 | 5 | 30 | 86.0 | 3.4 | 0.4 | 9.1 | 0.9 | 0.1 |  | 0.1 | 96.2 |
| 275 | 20 | 60 | 61.6 | 7.0 | 1.1 | 23.3 | 3.6 | 1.0 | 2.2 | 0.2 | 89.8 |
| 275 | 20 | 30 | 68.7 | 4.8 | 0.9 | 18.6 | 3.6 | 1.0 | 2.1 | 0.3 | 93.4 |
| 275 | 20 | 15 | 77.4 | 3.2 | 0.7 | 13.7 | 2.8 | 0.9 | 1.3 |  | 96.1 |

Examination of the data in Table 2 shows that the reactions parameters can be adjusted to maximize CFC-114 and minimize CFC-114a.

EXAMPLE 2

The same reactor as used in Example 1 was charged with 28.3 g (30 mL) of 2% Co on fluorided alumina prepared as described in U.S. Pat. No. 4,766,260. A mixture containing $CClF_2CClF_2$ (CFC-114, 88.1%) and $CCl_2FCF_3$ (CFC-114a, 11.9%) and HCl was fed to the reactor. The $HCl:C_2Cl_2F_4$ molar ratio was 20:1. For runs at 31, 38, 89, 90, and 93 hours, oxygen was added to the feed with the following molar ratios; $HCl:C_2Cl_2F_4:O_2=20:1:0.2$. The reaction temperature varied between 200° and 275° C., and the contact time was 30 seconds except for the 112 hour run where it was 15 seconds. The results of this run, in mole %, are shown in Table 3.

TABLE 3

| Hrs. | Temp. °C. | 114 | 114a | 113 | 113a | 112/a | 111 | PCE | 114/(114 + 114a) |
|---|---|---|---|---|---|---|---|---|---|
| 0 | FEED | 88.1 | 11.9 |  |  |  |  |  | 88.1 |
| 31 | 275 | 50.3 | 10.7 | 1.3 | 29.7 | 3.9 | 1.3 | 1.8 | 82.6 |
| 38 | 275 | 55.5 | 9.4 | 1.3 | 26.5 | 3.9 | 1.4 | 1.7 | 85.6 |
| 66 | 225 | 77.8 | 3.2 | 0.7 | 14.0 | 2.9 | 1.1 | 0.4 | 96.1 |
| 69 | 200 | 83.1 | 2.1 | 0.4 | 11.4 | 2.1 | 0.8 | 0.0 | 97.5 |
| 85 | 200 | 83.7 | 2.0 | 0.4 | 11.1 | 1.9 | 0.8 | 0.0 | 97.7 |
| 89 | 200 | 83.9 | 2.0 | 0.4 | 11.1 | 1.9 | 0.8 | 0.0 | 97.7 |
| 90 | 225 | 80.0 | 2.7 | 0.6 | 12.6 | 2.6 | 1.1 | 0.5 | 96.8 |
| 93 | 250 | 71.8 | 4.5 | 0.9 | 17.0 | 3.4 | 1.4 | 0.9 | 94.1 |
| 112 | 250 | 77.6 | 3.0 | 0.7 | 13.3 | 3.0 | 1.4 | 0.9 | 96.3 |

Particular embodiments of the invention are illustrated in the Examples. Other embodiments will become apparent to those skilled in the art from a consideration of the specification or practice of the invention. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the claims.

What is claimed is:

1. A process for enriching the amount of $CClF_2CClF_2$ relative to the amount of $CCl_2FCF_3$ from an initial mixture containing $CClF_2CClF_2$ and $CCl_2FCF_3$ comprising the steps of:

contacting said initial mixture with hydrogen chloride in the vapor phase at an elevated temperature in the presence of a vapor phase fluorination catalyst to produce a product mixture containing $C_2Cl_2F_4$ and chlorination products of $CCl_2FCF_3$ wherein the weight ratio of $CClF_2CClF_2$ to the total $C_2Cl_2F_4$ is higher than the weight ratio of $CClF_2CClF_2$ to the total $C_2Cl_2F_4$ in the initial mixture; and separating chlorinated products of $CCl_2FCF_3$ in the product mixture from the $C_2Cl_2F_4$ therein.

2. The process of claim 1 wherein the catalyst is selected from the group consisting of alumina, fluorided alumina, aluminum fluoride, metals supported on alumina, metals supported on aluminum fluoride, magnesium fluoride supported on aluminum fluoride, metals supported on fluorided alumina, alumina on carbon, aluminum fluoride on carbon, fluorided alumina on carbon, metals supported on carbon, chromium catalysts, mixtures including metal halides with aluminum fluoride and graphite, and chromium-magnesium optionally supported on graphite; said metals being selected from the group consisting of chromium, Group VIII metals, Group VIIB metals, Group IIIB metals, and zinc.

3. The process of claim 2 wherein the catalyst comprises aluminum fluoride.

4. The process of claim 2 wherein the initial mixture is contacted with HCl at a temperature from about 200° C. to 325° C., and wherein the molar ratio of HCl to $C_2Cl_2F_4$ in the initial mixture is from about 2:1 to 100:1.

5. The process of claim 2 wherein the $CCl_2FCF_3$ content of the initial mixture is equal to or greater than the $CClF_2CClF_2$ content.

6. The process of claim 5 wherein the fraction of total $C_2Cl_2F_4$ which is $CCl_2FCF_3$ is reduced by at least about 25%.

7. The process of claim 1, claim 2, or claim 6 wherein the initial mixture consists essentially of $CCl_2FCF_3$ and $CClF_2CClF_2$.

8. The process of claim 1, claim 2, or claim 6 wherein the $CClF_2CClF_2$ in the product mixture is at least 95% of the total $C_2Cl_2F_4$ content.

9. The process of claim 1, claim 2, or claim 6 wherein $CCl_3CF_3$ is the major chlorination product of $CCl_2FCF_3$.

10. The process of claim 9 wherein $CCl_3CF_3$ is separated from the $C_2Cl_2F_4$ in the product mixture by distillation.

11. A process for enriching the amount of $CClF_2CClF_2$ relative to the amount of $CCl_2FCF_3$ from an initial mixture containing $CClF_2CClF_2$ and $CCl_2FCF_3$ wherein the $CCl_2FCF_3$ content is equal to or greater than the $CClF_2CClF_2$ content, comprising the steps of:

contacting said initial mixture with hydrogen chloride in the vapor phase at an elevated temperature in the presence of a catalyst to produce a product mixture containing $C_2Cl_2F_4$ and chlorination products of $CCl_2FCF_3$ wherein the fraction of total $C_2Cl_2F_4$ which is $CCl_2FCF_3$ is reduced by at least about 25%; and separating chlorinated products of $CCl_2FCF_3$ in the product mixture from the $C_2Cl_2F_4$ therein; said catalyst being selected from the group consisting of fluorided alumina, aluminum fluoride, metals supported on aluminum fluoride, magnesium fluoride supported on aluminum fluoride, and metals supported on fluorided alumina, wherein said metals are selected from the group consisting of chromium, Group VIII metals, Group VIIB metals, Group IIIB metals, and zinc and the metal content of said supported metal catalysts is from about 0.1 to 10 percent by weight.

12. A process for enriching the amount of $CClF_2CClF_2$ relative to the amount of $CCl_2FCF_3$ from an initial mixture containing $CClF_2CClF_2$ and $CCl_2FCF_3$ wherein the $CCl_2FCF_3$ content is equal to or greater than the $CClF_2CClF_2$ content, comprising the steps contacting the initial mixture with HCl in the vapor phase at an elevated temperature from about 200° C. to 325° C., in the presence of a catalyst to produce a product mixture containing $C_2Cl_2F_4$ and chlorination products of $CCl_2FCF_3$ wherein the fraction of total $C_2Cl_2F_4$ which is $CCl_2FCF_3$ is reduced by at least about 25%; and separating chlorinated products of $CCl_2FCF_3$ in the product mixture from the $C_2Cl_2F_4$ therein; said catalyst being selected from the group consisting of fluorided alumina and cobalt on fluorided alumina and the molar ratio of HCl to $C_2Cl_2F_4$ in the initial mixture being from about 2:1 to 100:1.

13. The process of claim 12 wherein the catalyst is fluorided alumina.

14. The process of claim 12 wherein the catalyst is cobalt on fluorided alumina.

* * * * *